United States Patent [19]

Hester, Jr.

[11] Patent Number: 4,902,794
[45] Date of Patent: Feb. 20, 1990

[54] TRIAZOLO-BENZODIAZEPINES

[75] Inventor: Jackson B. Hester, Jr., Galesburg, Mich.

[73] Assignee: The Upjohn Company, Kalamazoo, Mich.

[21] Appl. No.: 515,884

[22] Filed: Jul. 20, 1983

Related U.S. Application Data

[63] Continuation of Ser. No. 317,618, Dec. 22, 1972, abandoned, which is a continuation-in-part of Ser. No. 201,207, Nov. 22, 1971, abandoned, which is a continuation-in-part of Ser. No. 138,278, Apr. 28, 1971, abandoned.

[51] Int. Cl.⁴ .................. C07D 487/04; A61K 31/55
[52] U.S. Cl. ..................................... 540/563; 514/220
[58] Field of Search ........................... 260/245.5

[56] References Cited

U.S. PATENT DOCUMENTS

Re. 28,505  8/1975  Hester ........................... 540/499
3,681,343   8/1972  Hester ........................... 260/245.5
4,427,590   1/1984  Allgeier et al. ............... 260/245.5

FOREIGN PATENT DOCUMENTS 2220612  11/1972  Fed. Rep. of Germany ...... 260/308
2220615  11/1972  Fed. Rep. of Germany ...... 260/308
6916543   5/1970  Netherlands .................... 260/245.5
7205705  10/1972  Netherlands .................... 260/308

Primary Examiner—Robert T. Bond
Attorney, Agent, or Firm—Robert A. Armitage; John T. Reynolds; Sidney B. Williams, Jr.

[57] ABSTRACT

1-Substituted-6-phenyl-4H-s-triazolo[4,3-a][1,4]benzodiazepines of the formula (III):

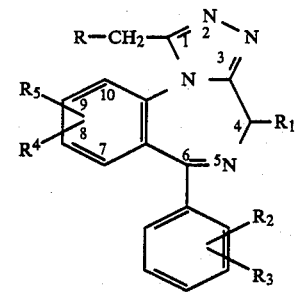

wherein R is selected from the group consisting of hydroxy, esters thereof, and alkoxy, in which the alkyl group is of 1 to 3 carbon atoms, inclusive; wherein $R_1$ is selected from the group consisting of hydrogen and alkyl of 1 to 3 carbon atoms, inclusive; and wherein $R_2$, $R_3$, $R_4$, and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino, and dialkylamino in which the carbon chain moieties are of 1 to 3 carbon atoms, inclusive, are produced by condensing a 1,3-dihydro-5-phenyl-2H-1,4-benzodiazepine-2-thione of the formula (I):

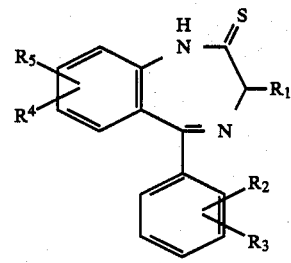

wherein $R_1$, $R_2$, $R_3$, $R_4$, and $R_5$ are defined as above, with an organic acid hydrazide of the formula (II):

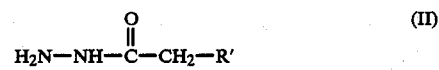

wherein R' is selected from the group consisting of hydroxy, and alkoxy defined as above. When R' is hydroxy, esters can be made in conventional manner.

The new products of formula III including their pharmacologically acceptable acid addition salts and N-oxides are useful as sedatives, tranquilizers and muscle relaxants in mammals and birds.

13 Claims, No Drawings

TRIAZOLO-BENZODIAZEPINES

BACKGROUND OF THE INVENTION

1. Field of the Invention

This invention is directed to new organic compounds and is particularly concerned with novel 1-substituted-6-phenyl-4H-s-triazolo4,3-a][1,4]benzodiazepines and a process for the production thereof.

The novel compounds and the process of production therefor can be illustratively represented as follows:

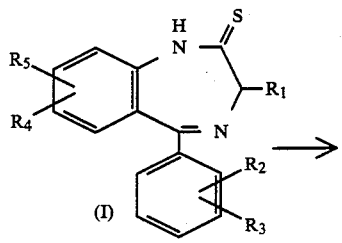

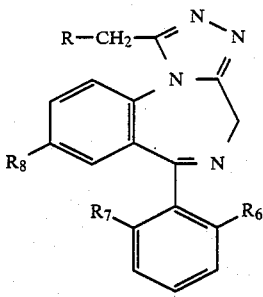

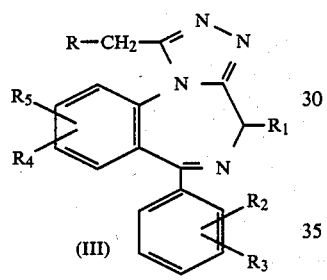

wherein R is selected from the group consisting of hydroxy and alkoxy in which alkyl is of 1 to 3 carbon atoms, inclusive;

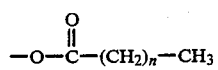

in which n is zero to 16,

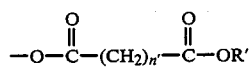

in which n' is 2 or 3, and R' is hydrogen or alkyl defined as above benzoyloxy acid, and phenylacetoxy acid; wherein $R_1$ is selected from the group consisting of hydrogen and alkyl of 1 to 3 carbon atoms, inclusive; and wherein $R_2$, $R_3$, $R_4$, and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino and dialkylamino in which the carbon chain moieties are of 1 to 3 carbon atoms, inclusive.

The more desirable products of this invention have the formula IV wherein R is selected from the group consisting of hydroxy and alkoxy of 1 to 3 carbon atoms, $R_6$ and $R_7$ are selected from the group consisting of hydrogen, fluorine, chlorine, bromine, and $NO_2$ and wherein $R_8$ is selected from the group consisting of hydrogen, fluorine, chlorine, bromine, $NO_2$, trifluoromethyl, and alkylthio in which alkyl is of 1 to 3 carbon atoms, inclusive.

Still more desirable are compounds of formula V below:

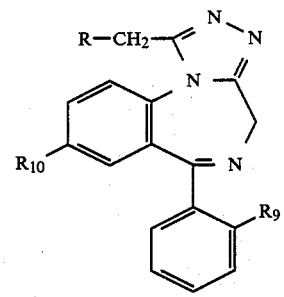

wherein R is selected from the group consisting of hydroxy and alkoxy of 1 to 3 carbon atoms, inclusive; and wherein $R_9$ and $R_{10}$ are selected from the group consisting of hydrogen and chlorine.

The invention includes also the esters of the compounds of formulae III, IV, and V wherein R is hydroxy.

Such esters are those of hydrocarbon carboxylic acids with 1 or 2 carboxyl groups.

For example alkanoic acids of 2 to 18 carbon atoms, inclusive such as acetic, propionic, butyric, valeric, hexanoic, enanthic, caprylic, pelargonic, capric, undecanoic, lauric, tridecanoic, myristic, pentadecanoic, palmitic, margaric, stearic acid; dibasic acids of 4 to 5 carbon atoms, inclusive, such as succinic, and glutaric acids and the aromatic acids of 7 to 8 carbon atoms e.g. benzoic and phenylacetic acids.

The invention further includes the pharmacologically acceptable acid addition salts and N-oxides of compounds of formula III, IV, or V and esters thereof.

The process of this invention comprises: condensing a 1,3-dihydro-5-phenyl-2H-1,4-benzoidazepine-2-thione of formula I in an organic solvent, e.g., a lower-alkanol of 1 to 4 carbon atoms, inclusive, or cyclohexanol with an acid hydrazide II, at a temperature between 60° and 120° C. to give the corresponding 1-substituted 6-phenyl-4H-s-triazolo[4,3-a][1,4]benzodiazepine (III, IV, or V).

Esters of the alcohols and acid addition salts or N-oxides of these compounds are prepared by known conventional means.

DESCRIPTION OF THE PREFERRED EMBODIMENT

Lower alkyl groups of 1 to 3 carbon atoms, inclusive, are exemplified by methyl, ethyl, propyl, and isopropyl.

The carbon chain moiety of alkoxy, alkylthio, alkylsulfinyl, alkylsulfonyl, dialkylamino which is of 1 to 3 carbon atoms, inclusive, is defined as lower-alkyl of 1 to 3 carbon atoms, inclusive, as above.

The alkanoylamino group of 1 to 3 carbon atoms consists of formamido

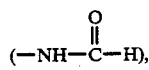

acetamido and propionamido.

The term halogen includes fluorine, chlorine, and bromine.

The novel compounds of the formula III including acid addition salts therof have sedative, tranquilizing and muscle relaxant effects in mammals and birds.

The acid addition salts of compounds of formula III contemplated in this invention, are the hydrochlorides, hydrobromides, hydriodides, sulfates, phosphates, cyclohexanesulfamates, methanesulfonates and the like, prepared by reacting a compound of formula III with an excess of the selected pharmacologically acceptable acid.

Sedative effects of 8-chloro-1-(hydroxymethyl)-6-phenyl-4H-s-triazolo[4,3-a][1,4]benzodiazepine (A) are shown by the following tests in mice:

Chimney test: [Med. Exp. 4, 145 (1961)]; The effective intraperitoneal dosage for 50% of the mice tested ($ED_{50}$) is 0.63 mg./kg. The test determines the ability of mice to back up and out of a vertical glass cylinder within 30 seconds. At the effective dosage, 50% of the mice failed doing it.

Dish test: Mice in Petri dishes (10 cm. diameter, 5 cm. higher, partially embedded in wood shavings), climb out in a very short itme, when not treated. Mice remaining in the dish for more than 3 minutes indicates tranquilization. The $ED_{50}$ equals the dose of test compound at which 50% of the mice remain in the dish. The $ED_{50}$ (intraperitoneal administration) in this test was 2.0 mg./kg.

Pedestal test: The untreated mouse leaves the pedestal in less than a minute to climb back to the floor of the standard mouse box. Tranquilized mice will stay on the pedestal for more than 1 minute. The $ED_{50}$ (intraperitoneal administration) is 1.56 mg./kg.

Nicotine antagonism test: Mice in a group of 6 are injected with the test compound-8-chloro-1-(hydroxymethyl)-6phenyl-4H-s-triazolo[4,3-a][1,4]benzodiazepine. Thirty minutes later the mice including control (untreated) mice are injected with nicotine salicylate (2 mg./kg.). The control mice show overstimulation, i.e., (1) running convulsions followed by (2) tonic extensor fits; followed by (3) death. An intraperitoneal dosage of 0.08 mg./kg. of the test compound protected 50% of the mice against (2) and against (3) 0.1 mg./kg. ($ED_{50}$) was necessary.

The following compound have (by intraperitoneal injection) an $ED_{50}$ as shown in the table below:

| COMPOUND | $ED_{50}$ (in mg./kg.) | | | |
|---|---|---|---|---|
| | Ch | D | P | Ni |
| 8-chloro-1-(ethoxymethyl)-6-phenyl-4H—s-triazolo[4,3-a]-[1,4]benzodiazepine (B) | 1.0 | 1.6 | 1.4 | 0.6 |
| 8-chloro-1-(hydroxymethyl)-6-(o-chlorophenyl)-4H—s-triazolo[4,3-a][1,4]benzodiazepine (C) | 0.04 | 0.03 | 0.03 | 0.032 |
| 8-chloro-1-(hydroxymethyl)-6-(o-chlorophenyl)-4H—s-triazolo[4,3-a][1,4]benzodiazepine hydrogen succinate (D) | 0.125 | 0.125 | 0.2 | 0.09 |

Ch = Chimney test
D = Dish test
P = Pedestal test
Ni = Nicotine antagonism (3) test The $LD_{50}$ for these compounds (A, B, and C in mice) is more than 100 mg./kg. and for the succinate (D) is more than 25 mg./kg.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose, and the like may be used as carriers or for coating purposes. Water and oil, e.g., coconut oil, sesame oil, safflower oil, cottonseed oil, peanut oil may be used for preparing solutions or suspensions of the active drug. Sweetening, coloring, and flavoring agents may be added.

For mammals and birds, food premixes, with starch, oatmeal, dried fishmeat, fishmeal flour, and the like can be prepared.

As tranquilizers, the compounds of formula III, IV, or V can be used in dosages 0.01 to 5 mg./kg. or preferably in a dosage of 0.05 mg. to 2 mg./kg. in oral or injectable preparations as described above, to alleviate tension and anxiety in mammals or birds, such as e.g., occurs when animals are shipped.

Other acid addition salts of the compound of formula III can be made, such as the fluosilicic acid addition salts which are useful mothproofing compounds or the trichloroacetates useful as herbicides against Johnson grass, Bermuda grass, yellow foxtail and green foxtail, and quack grass.

The starting materials of formula I of this invention, substituted or unsubstituted 1,3-dihydro-5-phenyl-2H-1,4-benzodiazepine-2-thiones, are described by G. A. Archer and L. H. Sternbach [J. Org. Chem. 29, 231 (1964) and U.S. Pat. No. 3,422,091]. These compounds (I) are made by the reaction of the known substituted or unsubstituted 1,3-dihydro-5-phenyl-2H-1,4-benzodiazepin-2-ones by heating with phosphorus pentasulfide in pyridine for about 45 minutes (Archer et al., ibid.). The following compounds of formula I are representative starting materials:

1,3-dihydro-5-phenyl-2H-1,4-benzodiazepine-2-thione;
6-chloro-1,3-dihydro-5-(m-bromophenyl)-2H-1,4-benzodiazepine-2-thione;
7-chloro-1,3-dihydro-5-phenyl-2H-1,4-benzodiazepine-2-thione;
8-chloro-1,3-dihydro-5-phenyl-2H-1,4-benzodiazepine-2-thione;
7-bromo-1,3-dihydro-5-phenyl-2H-1,4-benzodiazepine-2-thione;

7-chloro-1,3-dihydro-5-(3,4-dimethylphenyl)-2H-1,4-benzodiazepine-2-thione;
1,3-dihydro-5-(2-methyl-4-methoxyphenyl)-2H-1,4-benzodiazepine-2-thione;
9-bromo-1,3-dihydro-5-phenyl-2H-1,4-benzodiazepine-2-thione;
7-methyl-1,3-dihydro-5-phenyl-2H-1,4-benzodiazepine-2-thione;
7-nitro-1,3-dihydro-5-phenyl-2H-1,4-benzodiazepine-2-thione;
7-fluoro-1,3-dihydro-5-phenyl-2H-1,4-benzodiazepine-2-thione;
7-trifluoromethyl-1,3-dihydro-5-phenyl-2H-1,4-benzodiazepine-2-thione;
9-trifluoromethyl-1,3-dihydro-5-[p-(propionylamino)phenyl]-2H-1,4-benzodiazepine-2-thione;
7-cyano-1,3-dihydro-5-phenyl-2H-1,4-benzodiazepine-2-thione;
8-cyano-1,3-dihydro-5-[p-(trifluoromethyl)phenyl]-2H-1,4-benzodiazepine-2-thione;
7-chloro-1,3-dihydro-5-(o-chlorophenyl)-2H-1,4-benzodiazepine-2-thione;
6-ethylthio-1,3-dihydro-5-(o-bromophenyl)-2H-1,4-benzodiazepine-2-thione;
6,8-dichloro-1,3-dihydro-5-(o-fluorophenyl)-2H-1,4-benzodiazepine-2-thione;
8-propoxy-7-bromo-1,3-dihydro-5-[m-(ethylsulfinyl)phenyl]-2H-1,4-benzodiazepine-2-thione;
9-(diisopropylamino)-7-methyl-1,3-dihydro-5-[m-(propylsulfonyl)phenyl]-2H-1,4-benzodiazepine-2-thione;
7-bromo-1,3dihydro-5-(o-fluorophenyl)-2H-1,4-benzodiazepine-2-thione);
3-methyl-1,3-dihydro-5-(o-fluorophenyl)-2H-1,4-benzodiazepine-2-thione;
7-fluoro-1,3-dihydro-5-(o-fluorophenyl)-2H-1,4-benzodiazepine-2-thione;
3-ethyl-1,3-dihydro-5-(p-fluorophenyl)-2H-1,4-benzodiazepine-2-thione;
7-nitro-1,3-dihydro-5-(o-chlorophenyl)-2H-1,4-benzodiazepine-2-thione;
8-nitro-1,3-dihydro-5-(o-chlorophenyl)-2H-1,4-benzodiazepine-2-thione;
7-bromo-1,3-dihydro-5-(o-bromophenyl)-2H-1,4-benzodiazepine-2-thione;
7-methylsulfinyl-1,3-dihydro-5-(o-fluorophenyl)-2H-1,4-benzodiazepine-2-thione;
7-methyl-1,3-dihydro-5-(p-chlorophenyl)-2H-1,4-benzodiazepine-2-thione;
7-methylthio-1,3-dihydro-5-phenyl-2H-1,4-benzodiazepine-2-thione;
7-cyano-1,3-dihydro-5-(o-chlorophenyl)-2H-1,4-benzodiazepine-2-thione;
3,6,8-trimethyl-1,3-dihydro-5-(m-chlorphenyl)-2H-1,4-benzodiazepine-2-thione;
9-propylsulfonyl-7-methyl-1,3-dihydro-5-phenyl-2H-1,4-benzodiazepine-2-thione;
7-trifluoromethyl-1,3-dihydro-5-(o-chlorophenyl)-2H-1,4-benzodiazepine-2-thione;
7-dimethylamino-1,3-dihydro-5-phenyl-2H-1,4-benzodiazepine-2-thione;
7-fluoro-1,3-dihydro-5-(o-chlorophenyl)-2H-1,4-benzodiazepine-2-thione;
7,8-dicyano-1,3-dihydro-5-[p-(methylsulfonyl)phenyl]-2H-1,4-benzodiazepine-2-thione;
6,9-dichloro-1,3-dihydro-5-(p-isopropylphenyl)-2H-1,4-benzodiazepine-2-thione;
6,8-diethyl-1,3-dihydro-5-(m-ethylphenyl)-2H-1,4-benzodiazepine-2-thione;
6-nitro-1,3-dihydro-5-(o-propylthiophenyl)-2H-1,4-benzodiazepine-2-thione;
7,9-bis(dipropylamino)-1,3-dihydro-5-(o-nitrophenyl)-2H-1,4-benzodiazepine-2-thione;
9-acetylamino-1,3-dihydro-5-(p-cyanophenyl)-2H-1,4-benzodiazepine-2-thione;
and the like.

In carrying out the process of the invention, a selected 1,3-dihydro-5-phenyl-2H-1,4-benzodiazepine-2-thione (I) in an inert organic solvent, preferably in a lower-alkanol, e.g., 1-butanol, 2-butanol, hexanol, or the like is heated to between 60°–120° C., preferably to the reflux temperature of the mixture, with the selected acid hydrazide

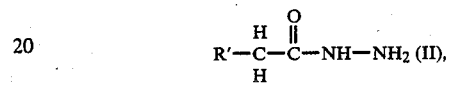

defined as above, during 2–48 hours. In the preferred embodiment of this invention the acid hydrazide is used in excess such as from 2 to 5 times the theoretically required amount, but the reaction is operative with smaller or larger amounts. The reaction period is between 2 and 18 hours. At the termination of the reaction the reaction mixture can be evaporated to give a crude product consisting of the desired 6-phenyl-4H-s-triazolo[4,3-a][1,4]benzodiazepine III. The crude compound III is then purified by standard methods, e.g. chromatography or recrystallization from solvents such as ethyl acetate, methylene chloride, chloroform, acetonitrile, methanol, ethanol, hexane, mixtures thereof, or the like.

The following examples are illustrative of the processes and products of the present invention, but are not to be construed as limiting.

EXAMPLE 1

8-Chloro-1-(ethoxymethyl)-6-phenyl-4H-s-triazolo[4,3-a][1,4]benzodiazepine

A solution of 1,3-dihydro-7-chloro-5-phenyl-2H-1,4-benzodiazepine-2-thione (5.74 g., 0.02 mole) and ethoxyacetic acid hydrazide (7.08 g., 0.06 mole) in n-butyl alcohol (300 ml.) was refluxed for about 3 hours with a slow stream of nitrogen bubbling through the reaction mixture. The mixture was then cooled and concentrated in vacuo. The resulting residue was suspended in water and extracted with methylene chloride. The extract was dried over anhydrous potassium carbonate and concentrated to give a residue. Crystallization of this residue from methylene chloride-methanol gave 0.66 g. of recovered starting material. The mother liquor was concentrated and chromatographed on silica gel (400 g.) using 40% ethyl acetate-60% Skellysolve B hexanes to 100% ethyl acetate for elution. The product obtained from this column was crystallized from ethyl acetate-Skellysolve B hexanes to give 1.74 g. of 8-chloro-1-(ethoxymethyl)-6-phenyl-4H-s-triazolo[4,3-a][1,4]benzodiazepine of melting point 168°–170° C. The analytical sample had a melting point of 168°–169° C.

Anal. calcd. for $C_{19}H_{17}ClN_4O$: C, 64.68; H, 4.86; Cl, 10.05; N, 15.88. Found: C, 64.70; H, 4.72; Cl, 9.98; N, 15.50, 15.99.

EXAMPLE 2

8-Nitro-1-(ethoxymethyl)-6-(o-chlorpohenyl)-4H-s-traizolo[4,3-a][1,4]benzodiazepine In the manner given in Example 1, a solution of 1,3-dihydro-7-nitro-5-(o-chlorophenyl)-2H-1,4-benzodiazepine-2-thione in n-butyl alcohol was heated to reflux with ethoxyacetic acid hydrazide to give 8-nitro-1-(ethoxymethyl)-6-(o-chlorophenyl)-4H-s-triazolo[4,3-a][1,4]benzodiazepine.

EXAMPLE 3

8-chloro-1-(methoxymethyl)-6-(o-chlorophenyl)-4H-s-triazolo4,3-a][1,4]benzodiazepine In the manner given in Example 1, a solution of 1,3-dihydro-7-chloro-5-(o-chlorophenyl)-2H-1,4-benzodiazepine-2-thione in n-butyl alcohol was heated to reflux with methoxyacetic acid hydrazide to give 8-chloro-1-(methoxymethyl)-6-(o-chlorophenyl)-4H-s-triazolo[4,3-a][1,4]benzodiazepine.

EXAMPLE 4

7-Fluoro-1-(methoxymethyl)-6-(o-bromophenyl)-4H-s-triazolo[4,3-a][1,4]benzodiazepine In the manner given in Example 1, a solution of 1,3-dihydro-6-fluoro-5-(o-bromophenyl)-2H-1,4-benzodiazepine-2-thione in n-butyl alcohol was heated to reflux with methoxyacetic acid hydrazide to give 7-fluoro-1-(methoxymethyl)-6-(o-bromophenyl)-4H-s-triazolo[4,3-a][1,4]benzodiazepine.

EXAMPLE 5

7-Trifluoromethyl-1-(propoxymethyl)-6-[m-(methylsulfonyl)phenyl]-4H-s-triazolo[4,3-a][1,4]benzodiazepine In the manner given in Example 1, a solution of 1,3-dihydro-6-trifluoromethyl-5-[m-(methylsulfonyl)phenyl]-2H-1,4-benzodiazepine-2-thione in n-butyl alcohol was heated to reflux with propoxyacetic acid hydrazide to give 7-trifluoromethyl-1-(propoxymethyl)-6-[m-(methylsulfonyl)phenyl]-4H-s-triazolo[4,3-a][1,4]benzodiazepine.

EXAMPLE 6

9-bromo-1-(methoxymethyl)-6-(2,6-difluorophenyl)-4H-s-triazolo[4,3-a][1,4]benzodiazepine In the manner given in Example 1, a solution of 1,3-dihydro-8-bromo-5-(2,6-difluorophenyl)-2H-1,4-benzodiazepine-2-thione in n-butyl alcohol was heated to reflux with methoxyacetic acid hydrazide to give 9-bromo-1-(methoxymethyl)-6-(2,6-difluorophenyl)-4H-s-triazolo[4,3-a][1,4]benzodiazepine.

EXAMPLE 7

7-Ethylsulfinyl-1-(isopropoxymethyl)-6-[p-(trifluoromethyl)phenyl]-4H-s-triazolo[4,3-a][1,4]benzodiazepine In the manner given in Example 1, a solution of 1,3-dihydro-6-ethylsulfinyl-5-[p-(trifluoromethyl)phenyl]-2H-1,4-benzodiazepine-2-thione in n-butyl alcohol was heated to reflux with isopropoxyacetic acid hydrazide to give 7-ethylsulfinyl-1-(isopropoxymethyl)-6-[p-(trifluoromethyl)phenyl]-4H-s-triazolo[4,3-a][1,4]benzodiazepine.

EXAMPLE 8

9-Methyl-1-(methoxymethyl)-6-(p-isopropylphenyl)-4H-s-triazolo[4,3-a][1,4]benzodiazepine In the manner given in Example 1, a solution of 1,3-dihydro-8-methyl-5-(p-isopropylphenyl)-2H-1,4-benzodiazepine-2-thione in n-butyl alcohol was heated to reflux with methoxyacetic acid hydrazide to give 9-methyl-1-(methoxymethyl)-6-(p-isopropylphenyl)-4H-s-triazolo[4,3-a][1,4]benzodiazepine.

EXAMPLE 9

7,9-Diethyl-1-(ethoxymethyl)-6-(2,4-diethylphenyl)-4H-s-triazolo[4,3-a][1,4]benzodiazepine In the manner given in Example 1, a solution of 1,3-dihydro-6,8-diethyl-5-(2,4-diethylphenyl)-2H-1,4-benzodiazepine-2-thione in n-butyl alcohol was heated to reflux with ethoxyacetic acid hydrazide to give 7,9-diethyl-1-(ethoxymethyl)-6-(2,4-diethylphenyl)-4H-s-triazolo[4,3-a][1,4]benzodiazepine.

EXAMPLE 10

8-Chloro-1-(methoxymethyl)-6-phenyl-4H-s-riazolo4,3-a][1,4]benzodiazepine

In the manner given in Example 1, a solution of 1,3-dihydro-7-chloro-5-phenyl-2H-1,4-benzodiazepine-2-thione in n-butyl alcohol was heated to reflux with methoxyacetic acid hydrazide to give 8-chloro-1-(methoxymethyl)-6-phenyl-4H-s-triazolo[4,3-a][1,4]benzodiazepine.

EXAMPLE 11

8-Chloro-1-(hydroxymethyl)-6-(o-chlorophenyl)-4H-s-triazolo[4,3-a][1,4]benzodiazepine A solution of 1,3-dihydro-7-chloro-5-(o-chlorophenyl)-2H-1,4-benzodiazepine-2-thione (9.63 g., 0.03 mole) and hydroxyacetic acid hydrazide (6.66 g.) in n-butyl alcohol (300 ml.) was refluxed for about 15 hours with a slow stream of nitrogen bubbling through the reaction mixture for the first hour. The mixture was then cooled and concentrated in vacuo. The resulting residue was suspended in water treated with a little ether and allowed to crystallize. The solid was collected by filtration and dried in vacuo. Recrystallization of this material from methylene chloride-methanol gave 4.96 g. of melting point 239°–241° C., 1.58 g. of melting point 236°–239° C. and 0.365 g. of melting point 232°–236° C. of 8-chloro-1-(hydroxymethyl)-6-(o-chlorophenyl)-4H-s-triazolo[4,3-a][1,4]benzodiazepine. The analytical sample had a melting point of 239.5°–241° C.

Anal. calcd. for $C_{17}H_{12}Cl_2N_4O$: C, 56.86; H, 3.37; Cl, 19.74; N, 15.60. Found: C, 56.27; H, 3.28; Cl, 19.75; N, 15.55.

EXAMPLE 12

Hydrogensuccinate ester of 8-chloro-1-(hydroxymethyl)-6-(o-chlorophenyl)-4H-s-triazolo[4,3-a][1,4]benzodiazepine An intimate mixture of 8-chloro-1-(hydroxymethyl)-6-(o-chlorophenyl)-4H-s-triazolo[4,3-a][1,4]benzodiazepine (4.61 g., 0.013 mole) and succinic anhydride (2.6 g., 0.026 mole) was fused at 120°–140° for 5–10 minutes under reduced pressure. The cooled melt was crystallized from methanol-methylene chloride to give 4.59 g. of the hydrogen succinate ester of 8-chloro-1-(hydroxymethyl)-6-(o-chlorophenyl)-4H-s-triazolo[4,3-a][1,4]benzodiazepine of melting point 245°-248° C.

Anal. calcd. for $C_{21}H_{16}Cl_2N_4O_4$: C, 54.91; H, 3.51; Cl, 15.44: N, 12.20. Found: C, 55.00; H, 3.41; Cl, 15.45; N, 12.27.

EXAMPLE 13

8-Chloro-1-(hydroxymethyl)-6-phenyl-4H-s-triazolo[4,3-a][1,4]benzodiazepine

In the manner given in Example 11, a solution of 1,3-dihydro-7chloro-5phenyl-2H-1,4-benzodiazepine-2-thione in n-butyl alcohol was heated to reflux with hydroxyacetic acid hydrazide to give 8-chloro-1-(hydroxymethyl)-6-phenyl-4H-s-triazolo[4,3-a][1,4]benzodiazepine of melting point 204°-206.5° C.

Anal. calcd. for $C_{17}H_{13}ClN_4O$: C, 62.87; H, 4.03; Cl, 10.92; N, 17.25 Found: C, 62.66; H, 14.11; Cl, 10.93; N, 17.25.

EXAMPLE 14

9-Nitro-1-(hydroxymethyl)-6-(o-fluorophenyl)-4H-s-triazolo[4,3-a][1,4]benzodiazepine In the manner given in Example 11, a solution of 1,3-dihydro-8-nitro-5-(o-fluorophenyl)-2H-1,4-benzodiazepine-2-thione in n-butyl alcohol is heated to reflux with hydroxyacetic acid hydrazide to give 9-nitro-1-(hydroxymethyl)-6-(o-fluorophenyl)-4H-s-triazolo[4,3-a][1,4]benzodiazepine.

EXAMPLE 15

8-Trifluoromethyl-1-(hydroxymethyl)-6-(o-chlorophenyl)-4H-s-triazolo[4,3-a][1,4]benzodiazepine In the manner given in Example 1, a solution of 1,3-dihydro-7-trifluoromethyl-5-(o-chlorophenyl)-2H-1,4-benzodiazepine-2-thione and hydroxyacetic acid hydrazide in n-butyl alcohol was refluxed to give 8-trifluoromethyl-1-(hydroxymethyl)-6-(o-chlorophenyl)-4H-s-triazolo[4,3-a][1,4]benzodiazepine.

EXAMPLE 16

8-Nitro-1-(hydroxymethyl)-6-(o-chlorophenyl)-4H-s-triazolo[4,3-a][1,4]benzodiazepine In the manner given in Example 11, a solution of 1,3-dihydro-7-nitro-5-(o-chlorophenyl)-2H-1,4-benzodiazepine-2-thione and hydroxyacetic acid hydrazide in n-butylalcohol was refluxed to give 8-nitro-1-(hydroxymethyl)-6-(o-chlorophenyl)-4H-s-triazolo[4,3-a][1,4]benzodiazepine.

EXAMPLE 17

8-Fluoro-1-(hydroxymethyl)-6-(o-chlorophenyl)-4H-s-triazolo[4,3-a][1,4]benzodiazepine In the manner given in Example 11, a solution of 1,3-dihydro-7-fluoro-5-(o-chlorophenyl)-2H-1,4-benzodiazepine-2-thione and hydroxyacetic acid hydrazide in n-butyl alcohol was refluxed to give 8-fluoro-1-(hydroxymethyl)-6-(o-chlorophenyl)-4H-s-triazolo[4,3-a][1,4]benzodiazepine.

EXAMPLE 18

10-propylthio-1-(hydroxymethyl)-4-methyl-6-(2,6-diethylphenyl)-4H-s-triazolo[4,3-a][1,4]benzodiazepine In the manner given in Example 11, a solution of 1,3-dihydro-9-propylthio-3-methyl-5-(2,6-diethylphenyl)-2H-1,4-benzodiazepine-2-thione and hydroxyacetic acid hydrazide in n-butylalchol was refluxed to give 10-propylthio-1-(hydroxymethyl)-4-methyl-6-(2,6-diethylphenyl)-4H-s-triazolo[4,3-a][1,4]benzodiazepine.

EXAMPLE 19

7-(Methylsulfonyl)-9-bromo-1-(hydroxymethyl)-6-(m-fluorophenyl)-4H-s-triazolo[4,3-a][1,4]benzodiazepine In the manner given in Example 11, a solution of 1,3-dihydro-6-(methylsulfonyl)-8-bromo-5-(m-fluorophenyl)-2H-1,4-benzodiazepine-2-thione and hydroxyacetic acid hydrazide in n-butyl alcohol was refluxed to give 7-(methylsulfonyl)-9-bromo-1-(hydroxymethyl)-6-(m-fluorophenyl)-4H-s-triazolo[4,3-a][1,4]benzodiazepine.

EXAMPLE 20

9-(Ethylsulfinyl)-7-(diethylamino)-1-(hydroxymethyl)-6-(m-formamidophenyl)-4H-s-triazolo[4,3-a][1,4]benzodiazepine.

In the manner given in Example 11, a solution of 1,3-dihydro-8-(ethylsulfinyl)-6-(diethylamino)-5-(m-formamidophenyl)-2H-1,4-benzodiazepine-2-thione and hydroxyacetic acid hydrazide in n-butylalcohol was refluxed to give 9-(ethylsulfinyl)-7-(diethylamino)-1-hydroxymethyl)-6-(m-formamidophenyl)-4H-s-triazolo[4,3-a][1,4]benzodiazepine.

EXAMPLE 21

8-Chloro-1-(hydroxymethyl)-6-(o-chlorophenyl)-4H-s-triazolo[4,3-a][1,4]benzodiazepine acetate ester In a manner similar to Example 12, a mixture of 8-chloro-1-(hydroxymethyl)-6-(o-chlorophenyl)-4H-s-triazolo[4,3-a][1,4]benzodiazepine and acetic anhydride was heated on the water bath to give 8-chloro-1-(hydroxymethyl)-6-(o-chlorophenyl)-4H-s-triazolo[4,3-a][1,4]benzodiazepine acetate (ester).

EXAMPLE 22

8-Chloro-1-(hydroxymethyl)-6-phenyl-4H-s-triazolo[4,3-a][1,4]benzodiazepine propionate (ester)

In a manner similar to Example 12, a mixture of 8-chloro-1-(hydroxymethyl)-6-phenyl-4H-s-triazolo[4,3-a][1,4]benzodiazepine and propionic anhydride was heated on the water bath to give 8-chloro-1-(hydroxymethyl)-6-phenyl-4H-s-triazolo[4,3-a][1,4]benzodiazepine propionate (ester).

EXAMPLE 23

8-chloro-1-(hydroxymethyl)-6-phenyl-4H-s-triazolo[4,3-a][1,4]benzodiazepine hexanoate (ester)

In a manner similar to Example 12, a mixture of 8-chloro-1-(hydroxymethyl)-6-phenyl-4H-s-triazolo[4,3-a][1,4]benzodiazepine and hexanoic anhydride was heated on the water bath to give 8-chloro-1-(hydroxymethyl)-6-phenyl-4H-s-triazolo[4,3-a][1,4]benzodiazepine hexanoate (ester).

EXAMPLE 24

8-(Trifluoromethyl)-1-(hydroxymethyl)-6-(o-chlorophenyl)-4H-s-triazolo[4,3-a][1,4]benzodiazepine benzoate (ester)

In a manner similar to Example 12, a mixture of 8-(trifluoromethyl)-1-(hydroxymethyl)-6-(o-chlorophenyl)-4H-s-triazolo[4,3-a][1,4]benzodiazepine and benzoic anhydride was heated on the water bath to give 8-(trifluoromethyl-1-(hydroxymethyl)-6-(o-chlorophenyl)-

4H-s-triazolo[4,3-a][1,4]benzodiazepine benzoate (ester).

EXAMPLE 25

8-nitro-1-(hydroxymethyl)-6-(o-chlorophenyl)-4H-s-triazolo[4,3-a][1,4]benzodiazepine phenyl acetate (ester)

In a manner similar to Example 12, a mixture of 8-nitro-1-(hydroxymethyl)-6-(o-chlorophenyl)-4H-s-triazolo[4,3-a][1,4]benzodiazepine and phenylacetic anhydride was heated on the water bath to give 8-nitro-1-(hydroxymethyl)-6-(o-chlorophenyl)-4H-s-triazolo[4,3-a][1,4]benzodiazepine phenylacetate (ester).

EXAMPLE 26

10-Propylthio-4-methyl-1-(hydroxymethyl)-6-(2,6-diethylphenyl)-4H-s-triazolo[4,3-a][1,4]benzodiazepine hydrogen glutarate ester In a manner similar to Example 12, a mixture of 10-propylthio-4-methyl-1-(hydroxymethyl)-6-(2,6-diethylphenyl)-4H-s-triazolo[4,3-a][1,4]benzodiazepine and glutaric anhydride was heated on the water bath to give 10-propylthio-4-methyl-1-(hydroxymethyl)-6-(2,6-diethylphenyl)-4H-s-triazolo[4,3-a][1,4]benzodiazepine hydrogen glutarate (ester).

EXAMPLE 27

8-Chloro-1-(hydroxymethyl)-6-(o-chlorophenyl)-4H-s-triazolo[4,3-a][1,4]benzodiazepine butyrate (ester)

In a manner similar to Example 12, a mixture of 8-chloro-1-(hydroxymethyl)-6-(o-chlorophenyl)-4H-s-triazolo[4,3-a][1,4]benzodiazepine and butyric anhydride was heated on the water bath to give 8-chloro-1-hydroxymethyl-6-(o-chlorophenyl)-4H-s-triazolo[4,3-a][1,4]benzodiazepine butyrate (ester).

EXAMPLE 28

8-Chloro-1-(hydroxymethyl)-6-phenyl-4H-s-triazolo[4,3-a][1,4]benzodiazepine valerate (ester)

In a manner similar to Example 12, a mixture of 8-chloro-1-(hydroxymethyl)-6-phenyl-4H-s-triazolo[4,3-a][1,4]benzodiazepine and valeric anhydride were heated on the water bath to give 8-chloro-1-(hydroxymethyl)-6-phenyl-4H-s-triazolo[4,3-a][1,4]benzodiazepine valerate (ester).

EXAMPLE 29

8-Chloro-1-(hydroxymethyl)-6-(o-chlorophenyl)-4H-s-triazolo[4,3-a][1,4]benzodiazepine stearate In a manner similar to Example 12, a mixture of 8-chloro-1-(hydroxymethyl)-6-(o-chlorophenyl)-4H-s-triazolo[4,3-a][1,4]benzodiazepine and stearic anhydride was warmed in the steam bath to give 8-chloro-1-(hydroxymethyl)-6-(o-chlorophenyl)-4H-s-triazolo[4,3-a][1,4]benzodiazepine stearate ester.

In the manner given in the preceding examples 1–20, other 1,3-dihydro-5-phenyl-2H-1,4-benzodiazepine-2-thiones of formula I can be condensed with acid hydrazides of formula II, as defined earlier, to give other new 1-substituted 6-phenyl-4H-s-triazolo[4,3-a][1,4]benzodiazepines III, IV, or V. Representative compounds thus obtained include:

10-chloro-1-(methoxymethyl)-6-(m-isopropylphenyl)-4H-s-triazolo[4,3-a][1,4]benzodiazepine;
9-(dipropylamino)-1-(methoxymethyl)-6-[p-(propionyolamino)phenyl]-4H-s-triazolo[4,3-a][1,4]benzodiazepine;
8-(methylsulfinyl)-1-(ethoxymethyl)-6-(o-nitrophenyl)-4H-s-triazolo[4,3-a][1,4]benzodiazepine;
7-(ethylsulfonyl)-1-(propoxymethyl)-6-(o-cyanophenyl)-4H-s-triazolo[4,3-a][1,4]benzodiazepine;
4-propyl-1-(ethoxymethyl)-6-[m-(methylthio)phenyl]-4H-s-triazolo[4,3-a][1,4]benzodiazepine;
10-fluoro-7-chloro-1-(ethoxymethyl)-6-[p-(trifluoromethyl)phenyl]-4H-s-triazolo[4,3-a][1,4]benzodiazepine;
7,9-diethoxy-1-(methoxymethyl)-6-(m-ethoxyphenyl)-4H-s-triazolo[4,3-a][1,4]benzodiazepine;
8-(trifluoromethyl)-1-(ethoxymethyl)-6-phenyl-4H-s-triazolo[4,3-a][1,4]benzodiazepine;
8-Chloro-1-(methoxymethyl)-6-(o-fluorophenyl)-4H-s-triazolo[4,3-a][1,4]benzodiazepine;
1-(methoxymethyl)-6-(o-chlorophenyl)-4H-s-triazolo[4,3-a][1,4]benzodiazepine;
1-(ethoxymethyl)-6-phenyl-4H-s-triazolo[4,3-a][1,4]benzodiazepine;
8-fluoro-1-(methoxymethyl)-6phenyl-4H-s-triazolo[4,3-a][1,4]benzodiazepine;
8-nitro-1-(ethoxymethyl)-6-phenyl-4H-s-triazolo[4,3-a][1,4]benzodiazepine;
8-(acetylamino)-1-(hydroxymethyl)-6-[p-(trifluoromethyl)phenyl]-4H-s-triazolo[4,3-a][1,4]benzodiazepine;
4-propyl-1-(hydroxymethyl)-6-(o-cyanophenyl)-4H-s-triazolo[4,3-a][1,4]benzodiazepine;
4-ethyl-1-(hydroxymethyl)-6-[o-(ethylthio)phenyl]-4H-s-triazolo[4,3-a][1,4]benzodiazepine;
4-methyl-7,10-dichloro-1-(methoxymethyl)-6-(m-isopropoxyphenyl)-4H-s-triazolo[4,3-a][1,4]benzodiazepine;
9-(dipropylamino)-1-(propoxymethyl)-6-[m-(propylthio)phenyl]-4H-s-triazolo[4,3-a][1,4]benzodiazepine;
7-(diisopropylamino)-1-(hydroxymethyl)-6-[p-(dipropylamino)phenyl]-4H-s-triazolo[4,3-a][1,4]benzodiazepine;
8-chloro-1-(hydroxymethyl)-6-(3,4-dimethylphenyl)-4H-s-triazolo[4,3-a][1,4]benzodiazepine;
1-(hydroxymethyl)-6-(2-methyl-4-methoxyphenyl)-4H-s-triazolo[4,3-a][1,4]benzodiazepine;
8-(methylthio)-1-(isopropoxymethyl)-6-phenyl-4H-s-triazolo[4,3-a][1,4]benzodiazepine;
4,8-dimethoxy-1-(ethoxymethyl)-6-phenyl-4H-s-triazolo[4,3-a][1,4]benzodiazepine;
1-(hydroxymethyl)-6-(o-cyhlorophenyl)-4H-s-triazolo[4,3-a][1,4]benzodiazepine;
1-(hydroxymethyl)-6-phenyl-4H-s-triazolo[4,3-a][1,4]benzodiazepine;
8-chloro-1-(hydroxymethyl)-6-(o-fluorophenyl)-4H-s-triazolo[4,3-a][1,4]benzodiazepine;
8-bromo-1-(hydroxymethyl)-6-phenyl-4H-s-triazolo[4,3-a][1,4]benzodiazepine;
8-nitro-1(hydroxymethyl)-6-phenyl-4H-s-triazolo[4,3-a][1,4]benzodiazepine;
8-(trifluoromethyl)-1-(hydroxymethyl)-6-phenyl-4H-s-triazolo[4,3-a][1,4]benzodiazepine;
8-fluoro-1-(hydroxymethyl)-6-phenyl-4H-s-triazolo[4,3-a][1,4]benzodiazepine;
8-chloro-1-(hydroxymethyl)-6-(2,6-difluorophenyl)-4H-s-triazolo[4,3-a][1,4]benzodiazepine;
8-(methylthio)-1-hydroxymethyl-6-phenyl-4H-s-triazolo[4,3-a][1,4]benzodiazepine;
and the like.

As shown by examples 12 and 21 to 28, the acetates, propionates, butyrates, valerates, hexanoates, enanthates, caprylates, pelanganates, caprates, undecanoates, laurates, tridecanoates, myristates, pentadecanoates, palmitates, margarates, stearates, benzoates, phenylacetates, succinates, glutarates, and the like, are obtained when any of the above 1-(hydroxymethyl)-6-phenyl-4H-s-triazolo[4,3-a][1,4]benzodiazepines is heated with the corresponding selected acid anhydride. Representative compounds thus obtained include;

8-chloro-1-(hydroxymethyl)-6-(o-chlorophenyl)-4H-s-triazolo[4,3-a][1,4]benzodiazepine enanthate (ester);
8-chloro-1-(hydroxymethyl)-6-phenyl-4H-s-triazolo[4,3-a][1,4]benzodiazepine hydrogensuccinate (ester);
1-(hydroxymethyl)-6-(o-chlorophenyl)-4H-s-triazolo[4,3-a][1,4]benzodiazepine hydrogensuccinate (ester);
1-(hydroxymethyl)-6-phenyl-4H-s-triazolo[4,3-a][1,4]benzodiazepine acetate (ester);
8-nitro-1-(hydroxymethyl)-6-phenyl-4H-s-triazolo[4,3-a][1,4]benzodiazepine acetate (ester);
8-chloro-1-(hydroxymethyl)-6-(2,6-difluorophenyl)-4H-s-triazolo[4,3-a][1,4]benzodiazepine acetate (ester);
8-chloro-1-(hydroxymethyl)-6-(o-chlorophenyl)-4H-s-triazolo[4,3-a][1,4]benzodiazepine undecanoate (ester);
1-(hydroxymethyl)-6-(o-chlorophenyl)-4H-s-triazolo[4,3-a][1,4]benzodiazepine propionate (ester);
1-(hydroxymethyl)-6-o-chlorophenyl)-4H-s-triazolo[4,3-a][1,4]benzodiazepine palmatate (ester)
8-methylthio-1-(hydroxymethyl)-6-phenyl-4H-s-triazolo[4,3-a][1,4]benzodiazepine acetate (ester);
8-chloro-1-(hydroxymethyl)-6-phenyl-4H-s-triazolo[4,3-a][1,4]benzodiazepine stearate (ester);
8-chloro-1-(hydroxymethyl)-6-phenyl-4H-s-triazolo[4,3-a][1,4]benzodiazepine acetate (ester);

Pharmacologically acceptable acid addition salts or N-oxides are obtained from compounds of formula III, IV, or V and esters thereof by adding from 1 to 3 equivalents of a pharmacologically acceptable acid or peracid to a molar equivalent of the selected diazepine III, IV, or V or esters thereof. Preferably such addition may be made in a water-free medium e.g., ether, ethanol, or the like wherein the salt either precipitates or is collected by evaporation of the solvent. The hydrochlorides, hydrobromides, sulfates, phosphates, acetates, tartrates, citrates, sulfamates, N-5-oxides thereof, and the like are of particular interest in preparing pharmaceutical dosage forms.

I claim:

1. A 1-substituted 6-phenyl-4H-s-triazolo[4,3-a][1,4]benzodiazepine of the formula (III):

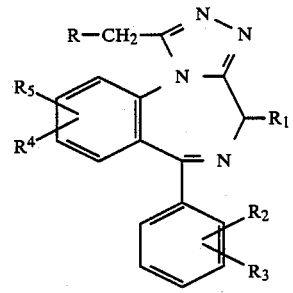

wherein R is selected from the group consisting of hydroxy and alkoxy, in which the alkyl moiety is of 1 to 3 carbon atoms, inclusive,

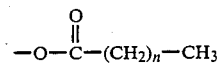

in which n is 0 to 16;

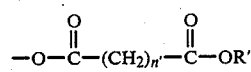

in which n' is 2 to 3 and R' is hydrogen, or alkyl defined as above, benzoyloxy, and phenylacetoxy; wherein $R_1$ is selected from the group consisting of hydrogen and alkyl of 1 to 3 carbon atoms, inclusive; and wherein $R_2$, $R_3$, $R_4$, and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino and dialkylamino in which the carbon chain moieties are of 1 to 3 carbon atoms, inclusive, and the pharmacologically acceptable acid addition salts thereof.

2. A 1-substituted-6-phenyl-4H-s-triazolo[4,3-a][1,4]benzodiazepine according to claim 1 of the formula (IV):

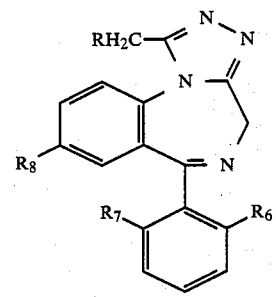

wherein R is selected from the group consisting of hydroxy and alkoxy of 1 to 3 carbon atoms, inclusive; wherein $R_6$ and $R_7$ are selected from the group consisting of hydrogen, fluorine, chlorine, bromine, and nitro; and wherein $R_8$ is selected from the group consisting of hydrogen, fluorine, chlorine, bromine, nitro, trifluoromethyl, and alkylthio in which the alkyl group is of 1 to 3 carbon atoms, inclusive; and the pharmacologically acceptable acid addition salts thereof.

3. A 1-substituted-6-phenyl-4H-s-triazolo[4,3-a][1,4]benzodiazepine of the formula (V):

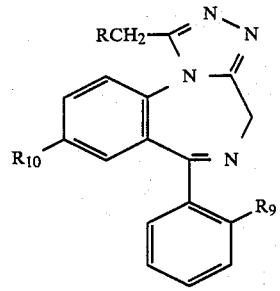

wherein R is selected from the group consisting of hydroxy and alkyloxy of 1 to 3 carbon atoms, inclusive; and wherein $R_9$ and $R_{10}$ are selected from the group consisting of hydrogen and chlorine, and the pharmaceutically acceptable acid addition salts thereof.

4. Esters of alkanoic acids of 2 to 18 carbon atoms, benzoic, phenylacetic, succinic, or glutaric acid with a compound of the formula

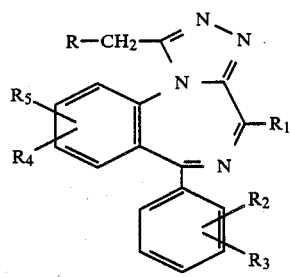

III wherein R is hydroxy and wherein $R_1$ is selected from the group consisting of hydrogen and alkyl of 1 to 3 carbon atoms, inclusive; and wherein $R_2$, $R_3$, $R_4$, and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino and dialkylamino in which the carbon chain moieties are of 1 to 3 carbon atoms, inclusive, and the pharmacologically acceptable acid addition salts thereof.

5. Ester of alkanoic acid of 2 to 18 carbon atoms, benzoic, phenylacetic, succinic or glutaric acid with a compound of the formula

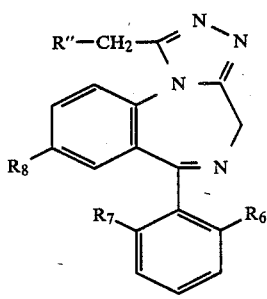

wherein R" is hydroxy; wherein $R_6$ and $R_7$ are selected from the group consisting of hydrogen, fluorine, chlorine, bromine, and nitro; and wherein $R_8$ is selected from the group consisting of hydrogen, fluorine, chlorine, bromine, nitro, trifluoromethyl, and alkylthio in which the alkyl group is of 1 to 3 carbon atoms, inclusive; and the pharmacologically acceptable acid addition salts thereof.

6. Ester or alkanoic acids of 2 to 18 carbon atoms, benzoic, phenylacetic, succinic, or glutaric acid with a compound of the formula

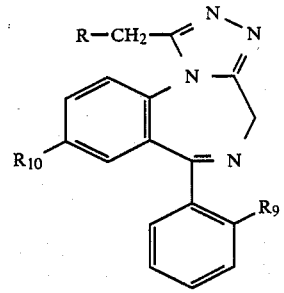

wherein R is hydroxy; $R_9$ and $R_{10}$ are selected from the group consisting of hydrogen and chlorine, and the pharmaceutically acceptable acid addition salts thereof.

7. The compound of claim 1 wherein R is methoxy, $R_1$, $R_2$, $R_3$, and $R_5$ are hydrogen and $R_4$ is 8-chloro and the compound is therefore 8-chloro-1-(methoxymethyl)-6-phenyl-4H-s-triazolo[4,3-a][1,4]benzodiazepine.

8. The compound of claim 3 wherein R is methoxy, $R_9$ and $R_{10}$ are chloro, and the compound is therefore 8-chloro-1-(methoxymethyl)-6-(o-chlorophenyl)-4H-s-triazolo[4,3-a][1,4]benzodiazepine.

9. The compound of claim 3 wherein R is ethoxy, $R_9$ is hydrogen and $R_{10}$ is chloro and the compound is therefore 8-chloro-1-(ethoxymethyl)-6-phenyl-4H-s-triazolo[4,3-a][1,4]benzodiazepine.

10. The compound of claim 1 wherein R is ethoxy, $R_1$, $R_3$, and $R_5$ are hydrogen, $R_2$ is o-chloro and $R_4$ is 8-nitro and the compound is therefore 8-nitro-1-(ethoxymethyl)-6-(o-chlorophenyl)-4H-s-triazolo[4,3-a][1,4]benzodiazepine.

11. 8-Chloro-1-(hydroxymethyl)-6-phenyl-4H-s-triazolo[4,3-a][1,4]benzodiazepine acetate ester.

12. 8-Chloro-1-(hydroxymethyl)-6-(o-chlorophenyl)-4H-s-triazolo[4,3-a][1,4]benzodiazepine hydrogen succinate ester.

13. 8-chloro-1-(hydroxymethyl)-6-(o-chlorophenyl)-4H-s-triazolo[4,3-a][1,4]benzodiazepine.

* * * * *